(12) United States Patent
Jackson

(10) Patent No.: US 11,436,939 B2
(45) Date of Patent: Sep. 6, 2022

(54) SYSTEM AND METHOD TO ACQUIRE MOST STATISTICALLY RELEVANT EDUCATIONAL, CAREER AND OTHER LIFE CHOICES

(71) Applicant: Douglas E. Jackson, Cary, NC (US)

(72) Inventor: Douglas E. Jackson, Cary, NC (US)

( * ) Notice: Subject to any disclaimer, the term of this patent is extended or adjusted under 35 U.S.C. 154(b) by 354 days.

(21) Appl. No.: 16/801,425

(22) Filed: Feb. 26, 2020

(65) Prior Publication Data

US 2020/0286400 A1    Sep. 10, 2020

Related U.S. Application Data

(60) Provisional application No. 62/814,071, filed on Mar. 5, 2019.

(51) Int. Cl.
| | |
|---|---|
| *G09B 19/00* | (2006.01) |
| *G06F 21/62* | (2013.01) |
| *G06F 16/2457* | (2019.01) |
| *G06N 7/00* | (2006.01) |
| *G06F 16/242* | (2019.01) |
| *G06F 16/23* | (2019.01) |
| *G09B 7/02* | (2006.01) |

(Continued)

(52) U.S. Cl.
CPC .......... *G09B 19/00* (2013.01); *G06F 16/2379* (2019.01); *G06F 16/2425* (2019.01); *G06F 16/24575* (2019.01); *G06F 21/6254* (2013.01); *G06F 40/30* (2020.01); *G06N 7/005* (2013.01); *G06Q 50/18* (2013.01); *G06Q 50/265* (2013.01); *G09B 7/02* (2013.01); *G16H 10/20* (2018.01); *G16H 10/60* (2018.01); *G16H 50/70* (2018.01)

(58) Field of Classification Search
CPC ........... G06F 16/24575; G06F 16/2379; G06F 16/2425; G06N 5/022; G06N 5/041; G06N 5/003; G16H 10/20; G16H 10/60; G06Q 50/18; G06Q 50/265; G09B 19/00
See application file for complete search history.

(56) References Cited

U.S. PATENT DOCUMENTS

| | | | |
|---|---|---|---|
| 7,472,110 B2 | 12/2008 | Achlioptas | |
| 8,473,984 B1 * | 6/2013 | Harmon | H04L 65/4076 |
| | | | 725/38 |

(Continued)

FOREIGN PATENT DOCUMENTS

WO    WO2006029149 A2    3/2006

*Primary Examiner* — Etienne P Leroux

(57) ABSTRACT

A method provides statistically reliable life experiences to guide a user to achieve personal goals related to education, career, and other life choice options. Based on the user's specific query, the method conducts searches and analyzes the search results for statistical significance. Internal anonymized databases containing life experiences and extensive external databases are used in the search and analysis. Subsequently the method sends the most relevant life experiences to the user with optional link to specific providers related with the query to the user for achieving the user's personal goals. The method may notify the user for lack of records/data and creates a survey to all users to contribute answers and/or life experiences to the specific query. Further, the method allows service providers and law enforcement personnel to conduct queries with specific purposes such as medical survey or criminal investigation with a subpoena.

14 Claims, 20 Drawing Sheets

(51) Int. Cl.
*G16H 10/60* (2018.01)
*G16H 50/70* (2018.01)
*G06Q 50/18* (2012.01)
*G06Q 50/26* (2012.01)
*G06F 40/30* (2020.01)
*G16H 10/20* (2018.01)

(56) References Cited

U.S. PATENT DOCUMENTS

| | | | |
|---|---|---|---|
| 9,262,517 B2 | 2/2016 | Kuhls | |
| 9,537,976 B2* | 1/2017 | Coffing | H04L 67/42 |
| 10,073,951 B2* | 9/2018 | Mohebbi | G16H 50/70 |
| 11,126,696 B1* | 9/2021 | Srivastava | G16H 40/20 |
| 2005/0216555 A1* | 9/2005 | English | G06Q 50/18 |
| | | | 709/204 |
| 2013/0036134 A1* | 2/2013 | Neven | G06V 40/172 |
| | | | 707/769 |
| 2013/0254213 A1 | 9/2013 | Cheng et al. | |
| 2013/0332219 A1* | 12/2013 | Clark | G06Q 10/1095 |
| | | | 705/7.19 |
| 2014/0280566 A1* | 9/2014 | Chen | H04L 63/10 |
| | | | 709/204 |
| 2016/0321935 A1 | 11/2016 | Mohler et al. | |
| 2016/0335543 A1* | 11/2016 | Goldstein | G16H 70/00 |
| 2016/0351000 A1* | 12/2016 | Zito, Jr. | G06F 3/0482 |
| 2017/0024796 A1* | 1/2017 | Fabo | G06Q 30/0631 |
| 2017/0097994 A1* | 4/2017 | Karavirta | G06F 16/23 |
| 2017/0323334 A1* | 11/2017 | Sheppard | G06Q 10/1057 |
| 2018/0013818 A1* | 1/2018 | Howard | H04W 4/023 |
| 2019/0042646 A1* | 2/2019 | Hoang | G06F 16/635 |
| 2019/0066136 A1* | 2/2019 | Kopikare | G06Q 30/0282 |
| 2019/0113973 A1* | 4/2019 | Coleman | G16H 50/20 |
| 2020/0311752 A1* | 10/2020 | Li | G06Q 30/0282 |
| 2021/0118531 A1* | 4/2021 | Kozloski | G06N 20/00 |

\* cited by examiner

User Contribution Key Table
(Sample)

| User_ID | Contribution-Key |
|---|---|
| USER-1 | ABCDEF |
| USER-2 | XYSDFD |
| USER-10 | MJDFDFFD |
| USER-11 | OJOJNNN |
| USER-12 | JOJJOO |
| ... | ... |
| ... | ... |
| ... | ... |
| USER-123898 | 12JBOSO |
| USER-123899 | 99454JD |

*[Unique] Contribution Keys can be randomly generated or generated any other way either daily, weekly, monthly, etc. and replaced in the *Internal Anonymized Database* records to:
--- ensure security of personal identifiable data if any information is ever breached to the public/hackers/disgruntled employees so they cannot connect it to actual individuals
--- will continuously allow Social Media web-site owner to maintain the foreign key between the actual end users, and, their data/answers they have contributed to the *Internal Anonymized Database*.

FIG. 18

Social Media *Internal Anonymized Database* comprises 10s of millions, 100s of millions to billions of member responses to 100s to 1000s of questions; questions created by other members' queries/requests for summarized/mined data.

Sample Table: Could be 1 of 100s of Physical or Virtual Database Tables

| Contribution Key | High School | College | College G.P.A. | HighSchool G.P.A. | Job #1 Title | Current Salary | Residence Zip | Birth Zip | High School Quarterback? |
|---|---|---|---|---|---|---|---|---|---|
| A3CDEF | Oak Hill | NYU | 3.65 | 3.85 | Sales | $100K | 12345 | 45678 | N |
| XYSDFD | Montgomery | Duke | 3.34 | 3.60 | CEO | $10M | 27123 | 09343 | N |
| MJDFDFFD | Ripley | UNC | 3.95 | 4.00 | SYSDEV | $80K | 14775 | 27500 | N |
| OIOINNN | Ft Myers | n/a | n/a | 2.65 | DRIVER | $40K | 34333 | NULL | Y |
| JOIJOO | Springfield | NCSU | 2.95 | 3.15 | n/a | n/a | NULL | 65223 | N |
| ... | ... | ... | ... | ... | ... | ... | ... | ... | ... |
| ... | ... | ... | ... | ... | ... | ... | ... | ... | ... |
| ... | ... | ... | ... | ... | ... | ... | ... | ... | ... |
| 1JJ8OSO | Mayville | MIT | 3.98 | 4.00 | WAITER | $20K | 14775 | 12598 | Y |
| 99454JD | Westfield | n/a | n/a | 3.00 | NULL | NULL | 14787 | n/a | N |

(1) "NULL" indicates the member has not answered the question.
(2) "n/a" indicates the member has answered but does not apply
(3) Contribution Keys get changed occasionally for security.
(4) Social Media website owner can allow end-users to add, delete and/or updated answers using foreign key (Contribution Key -> User_ID).

FIG. 19

SYSTEM AND METHOD TO ACQUIRE MOST STATISTICALLY RELEVANT EDUCATIONAL, CAREER AND OTHER LIFE CHOICES

The current application claims a priority to the U.S. Provisional Patent application Ser. No. 62/814,071 filed on Mar. 5, 2019.

FIELD OF THE INVENTION

The present invention relates to data processing. More specifically, the present invention relates to a query method that acquires valuable information containing the most statistically relevant life experiences including events and situations from a substantial number of individuals who purport to have already attained or experienced a target goal/situation. The relevant life experiences are not limited to a threshold number of replies or opinions that would otherwise results in bias or lack of substantial real-life experience. A user can benefit from this valuable information based on facts to better guide the decision making to attain specific educational, career and/or any other life goals/choices. Furthermore, using the valuable information, the query method optionally connects the user with various related providers to offer the user access to entities, products, and services to reach their goals as well as provide these providers more business. The present invention also provides for a constant, continuous feedback loop of information to the social network database via member surveys to acquire any missing information.

BACKGROUND OF THE INVENTION

Social networks including, but not limited to, LinkedIn®, Facebook®, Instagram®, Twitter®, etc., seek to link specific individuals with other people or news stories that have some common interest, experience, location, political view, etc. Usually, members of these social networks can communicate with one another only when permission is granted by one or both members with text messages, graphics, videos and/or photos. A major drawback to the usefulness of these social networks for a user seeking advice or help is that it is often limited to the user's lists of contacts or "followers", and, even then only to those individuals willing to take the time to give individual answers or advice to questions posted. Any advice or help given can hardly be considered objective, relied upon to be from actual experience, or the kind that one gathers from polling thousands or millions of people for their advice and actual experience. Even if one were to receive advice from hundreds or more people in current social networks, it would be far too time-consuming or nearly impossible to wade through, compare and rank all of the responses to make an informed choice, and, one would be missing the advice from every other potential option not mentioned.

High school students, college students, individuals considering going back to school, individuals considering switching career paths and/or even a young woman trying to decide who in her class she could go to the prom with (who will be the most likely to be successful in their life and she wants to be there to share it) want to get a specific list of the most likely/valuable colleges, majors, jobs, marital status or candidates to choose from to get them there. A perfect source of such information is a specific list gathered from the hundreds of millions of pieces of non-personally-identifiable-information (herein "NPII") contained in the information gathered from its millions of social network members (hereafter "social network database"), i.e. from when they signed up, from continued updates via social network member surveys, and even from public or purchase data sources i.e. average salaries of different job families, top 100 companies to work for, best places to live in the U.S., etc.

The social network database not only contains current information, but it can be viewed as containing millions of educational-paths, career-paths, and life-experience-paths through time with both successes and failures to draw from. Utilizing this information, millions of users can seek advice getting actual, objective guidance from the facts gathered from the lives, choices and careers of millions of the people who have gone before them, as opposed to getting tainted and subjective advice and/or other guidance directly from isolated individuals/friends, universities or businesses with limited experiences and/or biased opinions.

The social network database can be utilized to discover the most likely and very specific life events and choices made for target job titles (i.e. chief executive officer "CEO"), professions (i.e. how to become a judge, brain surgeon or astronaut) or particular salary ranges to lead someone from one crossroad in life to wherever they want to go through the use of proper statistics gathering, data mining techniques and data models including, but not limited to, decision trees, regression nodes, and neural networks, etc., all without compromising the anonymity of its members' information.

Social network members will gain substantial insights and options from the ability to select and query such NPII, assuming that the social network providers invest substantially into providing such services. Social network providers will invest substantially into providing such services because business and educational advertisers will likely pay hundreds of millions of advertising dollars and/or finder-fees to the social network providers to have direct web or other electronic links inserted whenever their businesses or institutions fit the results of any queries made by its social network members, and, potentially hundreds of millions of dollars in licensing/network usage fees for other entities to be granted access to search member profiles for specific medical or legal research.

Most social networks today are completely "free" (zero cost) to its members while a majority of the revenue is driven by advertising revenue from companies or individuals attempting to assign likely products that members may want to purchase based on their searches, physical locations, what their contacts have recommended, etc. There is enormous competition and a plethora of opportunities for undergraduate and graduate universities and colleges across the world to (pay fees to social network sites to) create targeted real-time advertising to individuals requesting advice on specific career paths and fields of study, especially when a particular university can get listed by such searches as one of the top universities producing highly-paid doctors, veterinarians, dentists, lawyers, CEOs, etc. Analytic data models and statistics have been highly used in the financial services arena for decades in determining credit scores, likelihoods of credit default and insurance risks in making financial loan and insurance premium decisions as well as determining whether to place a hold on deposited checks or a real-time decision on allowing a credit card transaction. These modeling methodologies can be used to create data models for "career advice" if the proper data points are given for one or all of these social network databases.

Alternative social network data inputs can be initiated by choice or by law from credit card companies, credit unions, PayPal® and banks whereas any weapons or explosive materials purchased, or, suspicious foreign transactions (hereafter "transactions of legal interest") made could be reported to all major social networks (to their private database) exactly like these financial entities currently report lines of credit loans, to credit reporting agencies, except that the reports need to be immediate, not once a month. Retail establishments and weapons' show vendors could be made to also report such transactions if made by cash, check or money order—as any other type would be taken care of by a financial institution—assuming all sales of such types are flagged to the supporting financial institution via the transaction details. This information would be saved in a non-published database by each social network provider. Social network providers can divide their database(s) into four sections: (1) their main database containing all of their social network entered data; (2) a secondary "private" database potentially containing transactions of legal interest provided for or by third parties such as the Federal Bureau of Investigation (FBI), banks, Central Intelligence Agency (CIA), Department of Homeland Security (DHS), local police, state police, etc., that can often be matched to social network member profiles; (3) a private merged database of (1) and (2) above with a unique, cross-referenceable key that only the social network owners can decipher/use to identify specific individuals; (4) an NPII database extracted from (3) above for the purpose of applying data models and third party queries, providing a cross-referenceable unique key created and replaced by the social network owner on a daily or weekly basis so that no external third party can determine or extract the identity of social network members by looking at the data in the NPII database.

To assist with anti-terrorism suspect searches, the social network owners can license out time and/or query capabilities against their NPII so that the DHS or other government agencies can either directly search, or what would be safer for privacy/fourth amendment issues, provide the social network owners an analytic model, i.e. a decision tree, neural network, regression node, etc., in a specified programming language, i.e. C, SAS, Java, etc., based on the NPII database metadata layout provided by the social network administrators with the proper input and output parameters for the social network administrators to run internally. The social network should only reveal the actual names, addresses, etc., of the results of such a search/data model result set if the final count of the search is a reasonable number, i.e., 20 individuals, and, a warrant is provided showing that the probable cause can be provided to the social network owners by the DHS or other government agency. For example, the DHS can provide a data model that scores individuals on where an individual grew up, has a recent weapon purchase, has an arrest record, no college degree, no church affiliation or has a social network connection with any zealous religious member, is single, has posted a message on their own or some other site related to a keyword like "revenge", "infidels", "kill", "was fired", etc. If the list of individuals returned is small, the social network owners could disclose, by warrant or law, the identities of these individuals to the DHS, FBI, etc. The combination of social and financial transaction searches could greatly advance law enforcement and help prevent mass violence.

Medical researchers can use queries of the social network database to find never-before-similarities, common living conditions, common foods eaten and/or cause-and-effect attributes for the masses with particular conditions, ailments, injuries, early death, longer-lifespans and/or even the ability to exercise/run into their 60s, 70s, 80s, or 90s. If particular research questions are not yet answered, the social media system can automatically add those survey questions to the thousands or millions of social media members' questionnaires. These social network database queries may be treated no different than queries that users may ask, or, analytic models or data mining requests may be made directly to the social network administrators similar to how law enforcement may provide such requests—except no PII data will be given to medial researches without express social network member consent.

Individuals trying to establish a career-goal or other life goal face thousands of career path choices, thousands of potential schools, hundreds of courses once in school and/or potentially thousands or even millions of people to befriend (or link with) in order to reach their goal, choosing many of which will likely result in failure or less than optimal outcomes while the person may only have one chance at making, or a limited time to make, the right choice in their lifetime. The choices are simply staggering. Similarly, companies and schools searching to reach the best hiring/attendee candidates have millions of potential people and companies to advertise in any of hundreds of marketing channels, many of which prove to give marginal payback on the money spent on that channel, and, law enforcement attempting to identify likely terrorists, often are ineffective in isolating their attention and resources to those most likely to cause harm out of thousands or tens of thousands of people that fit generic profiles or who are on watch-lists. For individuals seeking guidance, asking friends and acquaintances directly for advice gives extremely limited and biased feedback from extremely limited life experiences that may not even be on point. Just because an individual says they did something does not mean their history actually supports it. Social media sites also have difficulty gaining fees from members using their sites, and, often have trouble gaining new members on a large scale. Also, web site users are often bombarded with unrelated or semi-related advertisements that the users may or may not be interested in.

The current ability of social media site members to ask questions and query others' experiences is extremely limited as users usually only have access to a few dozen or few hundred direct individual contacts' opinions. Other websites, i.e. Neighbors®, allows generic questions to be posted to entire neighborhoods, but is still limited to the audience of who happens to look at that their email or text messages that day, who only provide limited information they want to give at that time, and often hide most relevant information to protect their privacy, as their name is often displayed with their responses. Getting facts from millions of individuals is far better than getting the opinion from a few dozen people as it will show the actions of thousands speak louder than the words of a few dozen. There is often not enough information in the social network database to answer specific questions that end-users or members ask. If that is the case, they usually do not provide a method of getting that information from the other members in the network who did not answer, or, from public database sources. The present invention's member surveys and querying of NPII data from all members provides far superior and reliable answers.

Social media websites such as, but not limited to, Facebook®, LinkedIn®, Twitter®, Snap-Chat®, etc., do not generally allow users access to summarized, NPII, statistics and relevance factors gathered from the millions of site members who have accomplished the goals at interest. This invention would allow a social media's users to view and prioritize all the choices and locations other site members have made on their career paths to reach/accomplish a desired goal. This access would also allow companies, schools and even law enforcement to be notified or to identify profiles of groups of individuals that have, or are likely to excel at a particular task, set of courses, or career. Users can make optimal and superior life choices from all who have gone before them, and, companies, schools and law enforcement can create targeted, cost-effective, search campaigns via the social media site. Individuals, schools, companies and law enforcement may pay the social media site additional fees for such services. Such fees, in total, would perhaps enrich the social media site owners and/or stockholders by hundreds of millions of U.S. dollars annually.

NPII can be gathered from the millions of site members and stored in a separate NPII database with only a unique foreign key, that could be changed daily for security reasons, linking the NPII records to the correct individual in order to keep track of which survey questions individuals answered, connect members with service providers, connect members with medical researchers, and, to help law enforcement gain access to the actual individuals' information as allowed by law. The invention also solves the semi-related mass advertising problem by providing users with extremely specific advertisements tailored to their specific queries i.e. to colleges, universities and companies they may not have known existed or provided the requested services.

Other patent-pending or patented inventions often only gather generic ideas to build on existing ideas to support a theoretical viewpoint based on the opinion of what some members have posted and ignore conflicting opinions and/or are often built on information having nothing to do with actual factual events. Others often rely on one or a few direct social member responses to questions instead of upon 1000s, 100,000s, or millions of factual data points; responses that are usually just a product of the other members' opinions at the time the question was asked, and therefore can change over time as well. Some other patents or patent-pending inventions may only allow categorization or statistics related to what the social media site itself preestablishes, or, what is actively being communicated between different users at the current time.

The present invention allows any user at any time to determine what is the appropriate categories are and provides the end-user with all (or many) of the most statistically relevant results and individual result frequencies at once, letting the end-user decide what result is best for them, instead of providing them with a single statistic of relevancy of a requested attribute or category.

Some other patents or patent-pending inventions may attempt to funnel answers to user queries into the most-closely matching paid service providers or paid advertises as determined by the social media software to make money, even if the results are not very close of a match to the query asked, whether or not that service provider or advertiser is really what the end-user really wants. The present invention will only match a paid advertiser or service provider if the results of an end-user query exactly matches or very closely matches the service provider or paid advertiser or is a subset of a greater category that matches the query. Other inventions that attempt to match "whatever is closest" will barrage the end-user with too much information and likely annoy them. Other patents or patent-pending inventions may attempt to gather information from the social network databases merely to expand members' social circles by matching their likes/dislikes, habits, past-times, past jobs, or other attributes they have in common. The goal of these inventions is completely different than this invention. The present invention is not used for members to connect to other members whom they do not currently know, but instead is used primarily to guide members through their lives via using the information from the lives of all other members who have gone before them (while optionally connecting them directly to the establishment or person they need to connect with to get there), and can also provide law enforcement and medical researchers with profiles of all members in the social network database that match particular search parameters without initially disclosing personal identifiable information (hereafter "PII"), without a valid, narrow-in-scope, subpoena.

SUMMARY OF THE INVENTION

The present invention is a method and system to provide most statistically relevant educational, career and other life choice options gathered from life experiences of millions of users such as social network members to guide a user towards their short-term and long-term life goals. The method of the present invention provides users with specific service provider's contact information for reaching those goals/answers, and conditionally provides service providers and/or law enforcement entities with the contact information of specific users whose profiles match pre-selected criteria provided by the providers and entities.

By reliably identifying optimal schools, majors, companies, careers, locations, people or other criteria, the method can attain life goals, connect users with service providers, and, allow service providers, law enforcement personnel and medical researchers to find user matching particular and generic profiles. The present invention implements a methodology to send survey questions to millions of users asking for information that is not currently provided, without overburdening users with thousands of questions at once. Each user would only be presented with a few questions at a time at each log-in time, or, each time when the user runs a query, in order to give them authorization to run a query themselves, or, giving them some monetary compensation in return. Any questions answered would be added to a plurality of internal databases without tying the user who answered them to the answers in any obvious way, but a cross-referencing key would be used and only identifiable by the method of the present invention. Also, the user would not be limited to using questions set up by the method as the user is enabled to ask questions related to any information gathered in the plurality of internal databases, or, any information that can be gathered in the future via surveys.

The method provides a very high level of graphical user interface to the user to access the present invention. If the user wants to access the anonymized internal database to ask a question or run a query, the method will check if the user is allowed to do so. Such permission may be given if the method allows a certain number of free queries, or, if the user pays a fee, or if the user has answered a select number of survey questions to fill in anonymized internal database. The user is either allowed, or not allowed, to query the anonymized internal database.

In the anonymized internal database, a unique foreign key value is used to link the private information to the user's PII (personal identifiable information) in what should be an encrypted database as well as a "contribution flag/key" herein ("contribution key") recorded for each survey question answered so the social media administrators/owners would know which questions each member has answered and which are fair game for upcoming surveys for that member. To prevent hackers or others from having access to PII about the life experience information contributed by each user and saved in the internal database, the foreign key values linking PII and NPII can be regenerated with different values every day, week, month, etc. The method thus records any contribution the user made to the internal databases and can use such contribution for any user's query of life choice and personal goals. Further, the method can use the anonymized internal databases to identify the user whose profile is identified, or, conditionally provided to law enforcement, medical researchers or service providers through queries.

The process of the method starts with the user entering a query that includes specific life choice and/or personal goals related to career, education, employment, healthcare, insurance, etc. Based on the query, the method searches the plurality of internal anonymized databases containing NPII and external databases that represent all publicly available data files and data such as census data, zip codes, city-state/province-country listings, pricing information, geocoding coordinates, voter records, weather forecasts or past weather data, etc. The method then analyzes the resulting search results which may comprise hundreds and/or thousands of life experiences of other users and/or individuals who may not be users of the present invention. These search results are analyzed for security, accuracy, and statistical significance. Subsequently the method sends the most statistically relevant life experiences to the user, i.e. the top 10 list of colleges and frequencies of attendance of each for a query asking for such information. The method, however, may notify the user for lack of records/data related to the specific query if the total number of statistically significant life experience records is less than a predetermined threshold number, 30, for instance. Simultaneously, the method creates a survey to all users to contribute answers and/or life experiences to the specific query. When sending life experience results to the user, the method can incorporate the information of specific providers who match the specific query and/or are related with the query results. Likewise, per the user's permission, the method may send the user's contact information to the relevant providers who can help the user with achieving personal goals.

BRIEF DESCRIPTION OF THE DRAWINGS

FIG. 18 is a diagram of an embodiment of a database structure used to anonymizing internal databases by the method of the present invention.

FIG. 19 is a diagram of an embodiment of an internal anonymized database managed by the method of the present invention.

DETAIL DESCRIPTIONS OF THE INVENTION

All illustrations of the drawings are for the purpose of describing selected versions of the present invention and are not intended to limit the scope of the present invention.

As can be seen in FIG. 1 to FIG. 20, the present invention comprises a system and method of providing statistically reliable life choice experiences to guide a user to achieve personal goals. The method of the present invention allows the user to query any life choices and goals including, but not limited to educational, career, business, financial, religious, spiritual, athletic, and/or any other life choice options. Based on the user's specific query and/or personal goals, the method acquires relevant life experiences of millions of other users, including, but not limited to, social network members, service providers, professors of colleges and universities, officers and executives of corporations, institutions, and government entities, etc. The method subsequently analyzes the relevant life experiences found and supplies the most statistically significant life experiences to guide the user towards their short-term and long-term life goals. Further, the method provides the user with specific service provider's contact information for reaching those goals/answers, and conditionally provides service provider and/or law enforcement users with contact data of other users whose profiles match pre-selected criteria specified by the provider users. The method of the present invention comprises a means for reliably identifying optimal schools, majors, companies, businesses, careers, locations, people or other criteria via a social network to help the user achieve life goals, connecting users with service providers, and, allowing service providers and law enforcement personnel to research users matching particular generic profiles. The present invention provides a methodology to send survey questions to thousands or even millions of end-users asking for information that is not currently provided otherwise without over-burdening the end-user with thousands of questions at that same time. Each user would only be presented with a few questions at a time when using the present invention, or, each time they want to run a query, in order to give them authorization to run a query themselves, or, giving them some monetary compensation in return. Any question answered would be added to the internal databases without tying the end-user who answered them in any obvious way. Rather, a cross-referencing key is used and only identifiable by the method and system of the present invention. Additionally, the end-user would not be limited to using questions set up by the present invention, as the method allows the user to ask questions related to any information gathered in any social media database, or, any information that can be gathered in the future via surveys.

Figure 1:
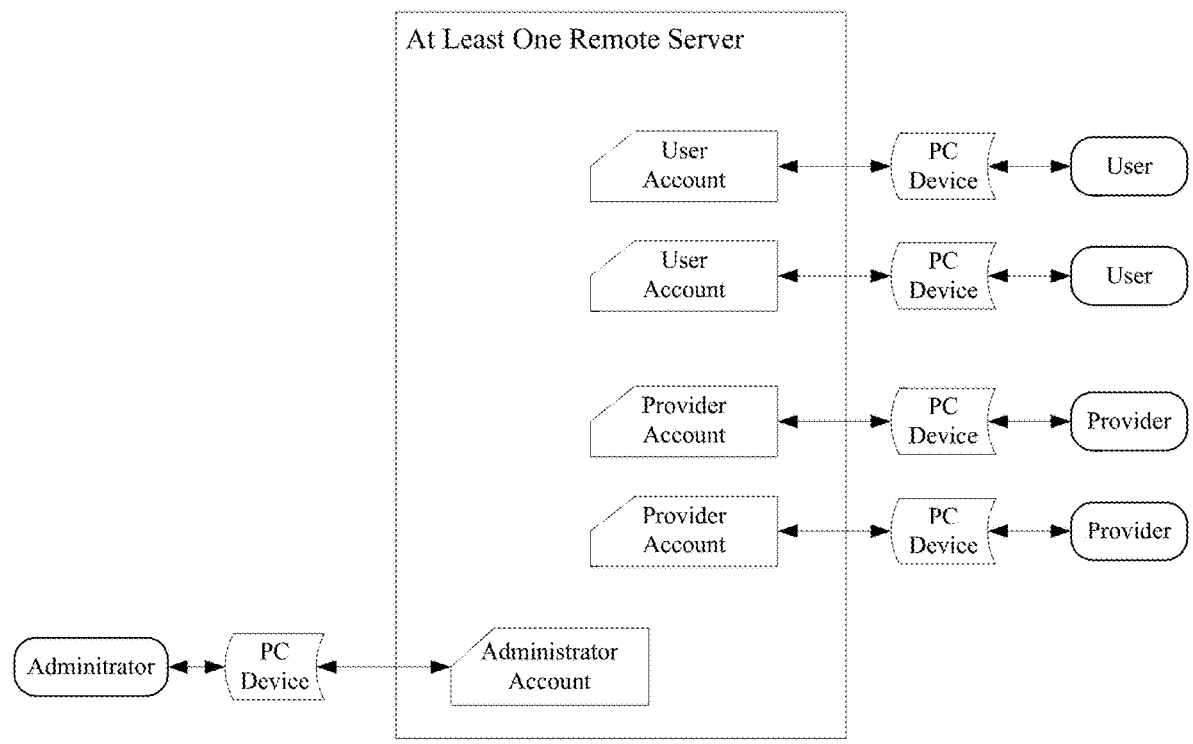
FIG. 1 is a system diagram of the present invention.
Figure 2:
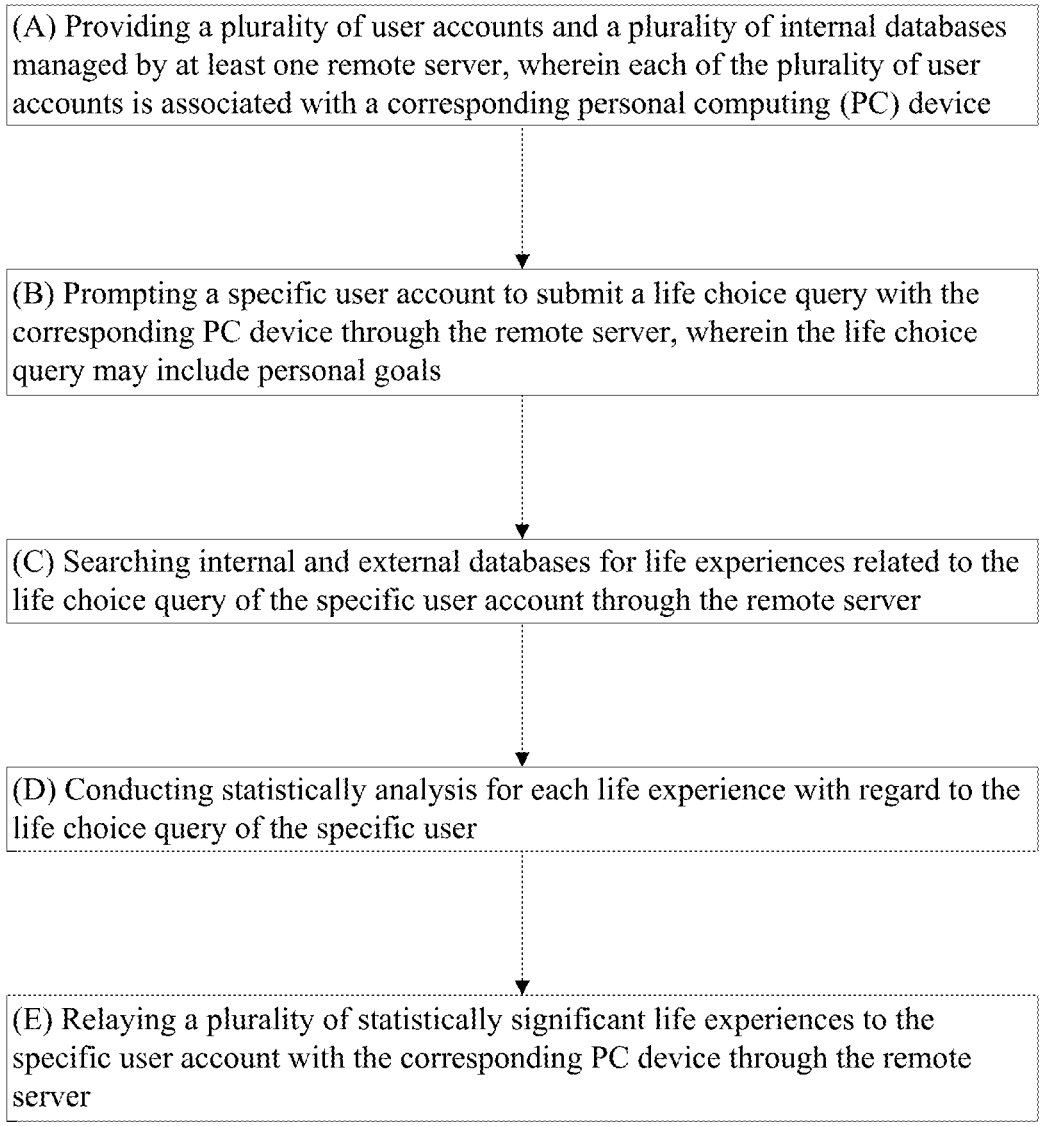
FIG. 2 is a flowchart of the overall process implemented by the method of the present invention.

As can be seen in FIG. 1, the method of the present invention comprises a system and method to offer statistically reliable life choice experiences to guide a plurality of users to achieve personal goals. To accomplish this, the method of the present invention associates each of the plurality of users with a unique account from a plurality of user accounts and a plurality of internal databases that are managed by at least one remote server (Step A), as seen in FIG. 2. Each of the plurality of user accounts is associated with a corresponding personal computing (PC) device. For the purposes of this invention, a PC device may also be defined as one or more processing threads operating on the behalf of the user from or to a virtual or physical server, or, virtual desktop session. The corresponding PC device allows the user to interact with the present invention and can include, but is not limited to, a smartphone, a smart watch, a laptop, a desktop, a server, a server computer, a cloud computing device, a server terminal, a tablet computer, mainframes smart appliances, "internet of things" (TOT) connected machines, home and commercial connected thermostats, connected refrigerators, televisions, cars, vehicular computer interfaces, connected watches, DVD players, etc. The corresponding PC device also can include any "server" machine. The corresponding PC device can get more sophisticated by the day, and often more personal, whereas in the near future a PC device also can be attached to or inside a user, user's clothing, or an accessory that the user wears or carries around. The users of the plurality of user accounts may include relevant parties such as, but are not limited to, individuals, social network members, officials, law enforcement personnel, professors, educators, education staff, medical professionals, doctors, health care providers, insurance agents, brokers, real estate professionals, financial professionals, entities, consumers, managers, business owners, companies, corporations, associations, organizations, government entities, colleges, universities, institutions, administrators, etc. Included in the plurality provider accounts are providers including, but not limited to, advertisers, advertisement organizations, marketing professionals, marketing corporations, officials, law enforcement personnel, police officers, police department, motor vehicle department, professors, educators, education staff, medical professionals, medical providers, doctors, health care providers, insurance agents, brokers, real estate professionals, financial professionals, sports centers, gyms, sports organizations, athletic associations, athletic training groups, entities, consumers, managers, business owners, companies, corporations, associations, organizations, government entities, colleges, universities, institutions, etc. Further, the at least one remote server is used to manage the system and method to provide statistically reliable life choice experiences to guide a user to achieve personal goals for the plurality of user accounts. The remote server can be managed through an administrator account by an administrator as seen in FIG. 1. The administrator who manages the remote server includes, but is not limited to, technician, engineer, system specialist, system administrator, software engineer, IT (information technology) specialist, IT professional, computer engineer, computer scientist, computer technologist, consultant, manager, owner, executive officer, chief operating officer, chief technology officer, chief executive officer, president, company, corporation, organization, association, etc. Moreover, the remote server is used to execute a number of internal software processes, fetch and store data for the present invention. The software processes may include, but are not limited to, server software programs, web-based software applications or browsers embodied as, for example, but not limited to, websites, web applications, desktop applications, cloud applications, mobile applications compatible with a corresponding user PC device, etc. Additionally, the software processes may store data into a plurality of internal databases and communicate with external databases, which may include, but are not limited to, user profile databases, personal information databases, anonymized social network databases, databases maintaining data about surveys, social network databases, large datasets for survey data, databases maintaining data about life experiences, databases maintaining data about professions, databases maintaining data about education, employment, finance, career, business, athletics, sports, personal goals, personal growth, spiritual/religious experiences, etc. The interaction with external databases over a communication network may include, but is not limited to, the Internet.

Figure 20:
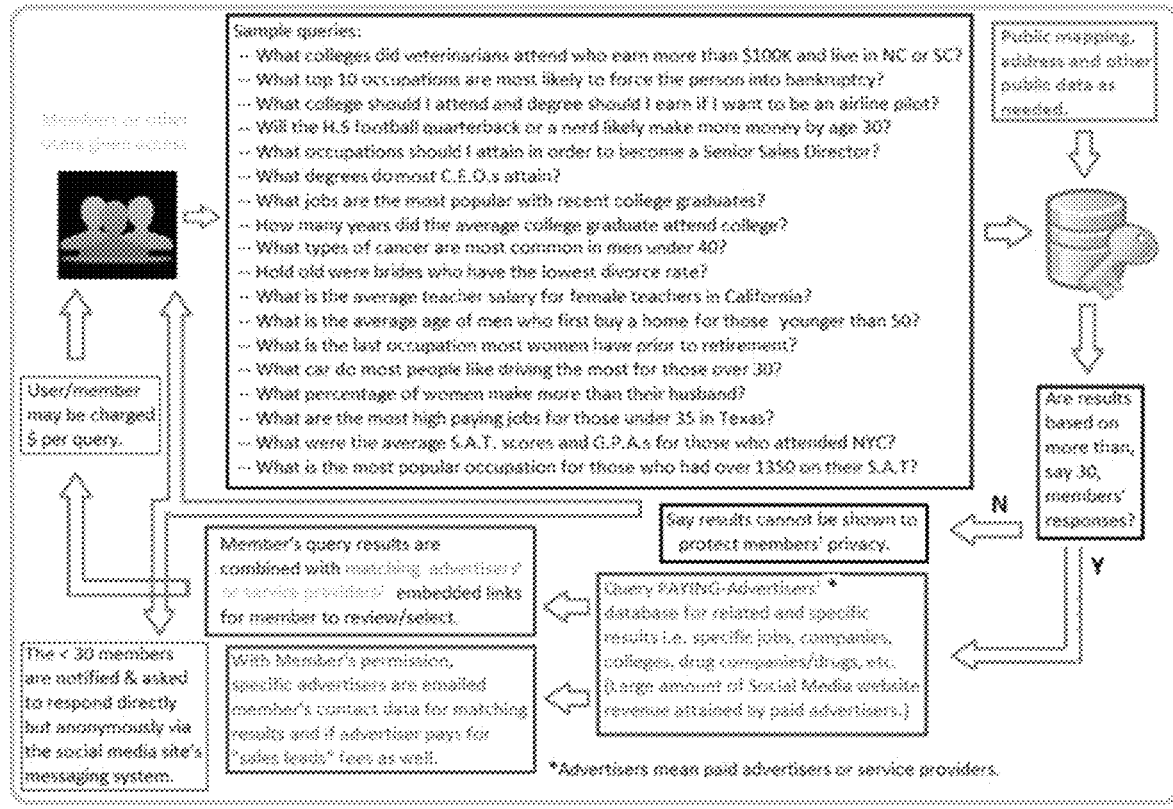
FIG. 20 is a flowchart of a sub-process for updating anonymized internal databases by the method of the present invention.

As can be seen in FIG. 2, the overall process of the method of the present invention prompts a specific user account to submit a life choice query with the corresponding PC device through the remote server, wherein the life choice query may include personal goals (Step B). More specifically, the method prompts the specific user to enter any query related to a life choice including, but not limited to, education, career, employment, personal growth, spiritual/religious growth, sports, athletics, life style, travel, finance, politics, etc. The query can include desired life goals or specific goals related to the life choice in question. For example, questions that the specific user may include in the query may be, "What colleges did veterinarians attend who earn more than $100,000 and live in NC (North Carolina)?" or "What are the highest paying jobs for those under 35 years-old in Texas?", "What was your G.P.A. (Grade Point Average) in high school?", "How old were you when you had your first car accident?", "Have you ever stole anything?", "How much weight did you gain in college?", etc., as can be seen in FIG. 20.

Subsequently, the method searches internal and external databases for life experiences related to the life choice query of the specific user account through the remote server (Step C). Specifically, the method conducts exclusive searches in the internal and external databases for relevant personal life experiences of other uses within the system and/or external social media/network systems. Additionally, the method may search external databases developed/maintained by and associated with organizations including, but not limited to, colleges, universities, public libraries, nonprofit organizations, research institutes, government entities, etc. As a result, the search may return substantial number of records, data sets, life experiences, survey reports, etc.

Once the search is complete, the method conducts statistical analysis for each life experience with regard to the life choice query of the specific user (Step D). When the number of relevant life experiences found through the search in Step C is greater than a threshold number, for example, 30, the method conducts statistical analysis to sort the significance of each record in relation to the query of the specific user. Multiple analysis techniques may be used in the method of the present invention, including, but not limited to, statistical modeling, data mining, artificial intelligence (AI) technology such as machine learning, neural network, etc. Subsequently, the method relays a plurality of statistically significant life experiences to the specific user account with the corresponding PC device through the remote server (Step E). The plurality of statistically significant life experiences includes the most relevant records to the query of the specific user and is sent to the specific user for guidance toward achieving desired life goals.

Figure 3:
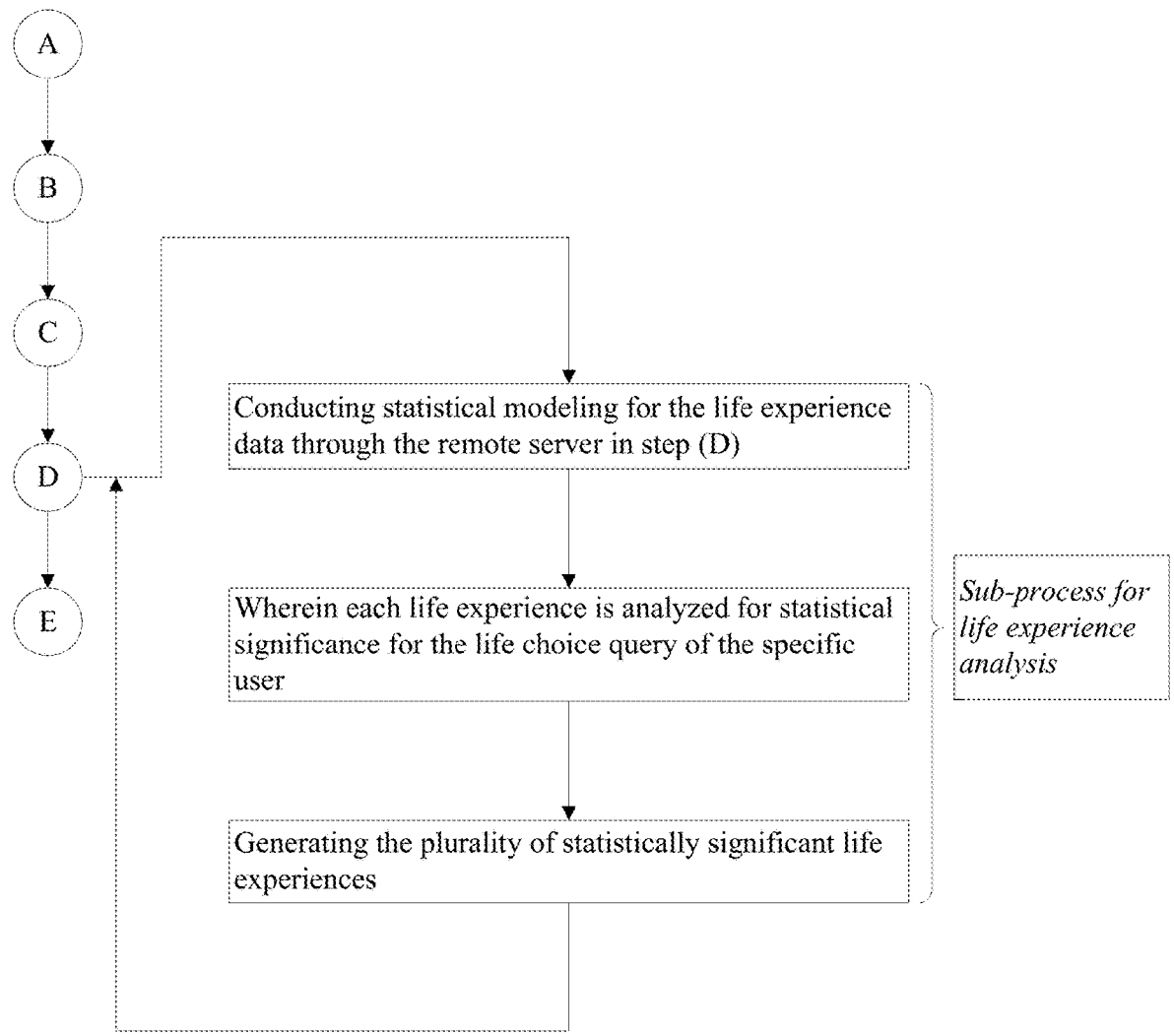
FIG. 3 is a flowchart of a sub-process for life experience analysis of the method of the present invention.
Figure 4:
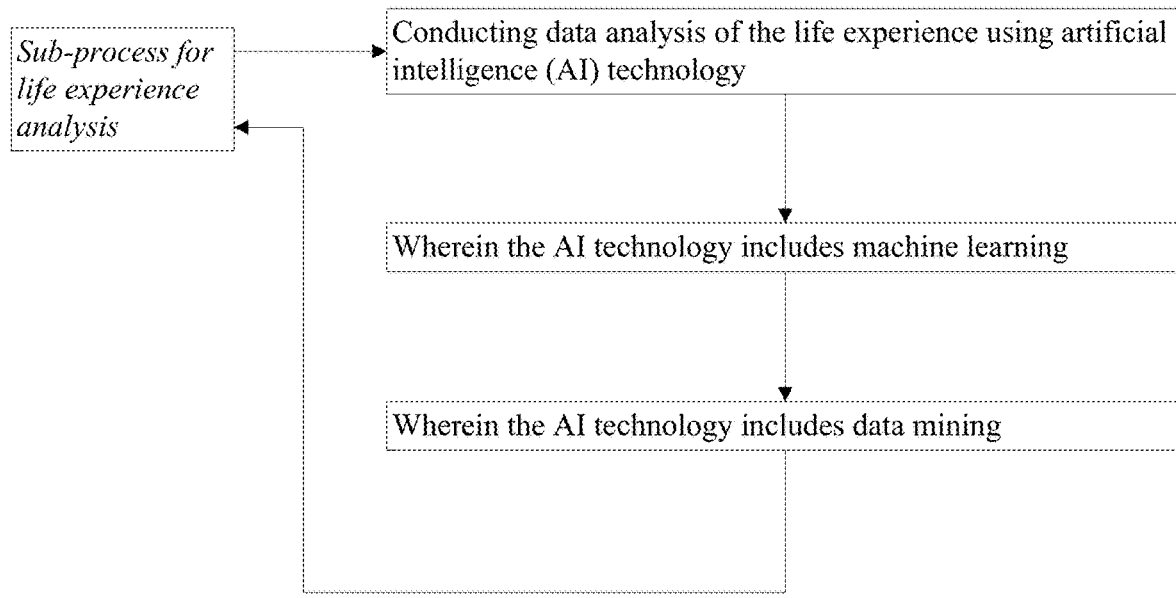
FIG. 4 is a flowchart of an alternative embodiment of the sub-process for life experience analysis of the method of the present invention.

As can be seen in FIG. 3, the method provides a sub-process for life experience analysis of the searched records for the specific user. More specifically, the method conducts statistical modeling for the life experience data through the remote server in Step D, wherein each life experience is analyzed for statistical significance for the life choice query of the specific user, thus generating the plurality of statistically significant life experiences. The method analyzes each life experience record found in Step C using various statistical and AI techniques for significance of relevance with the query of the specific user. Subsequently, the method ranks the records with respect to relevance and generate the plurality of life experience, of which the number of records is at least equal to the threshold number but may usually be a greater number. This plurality of most statistically significant life experiences is then relayed to the specific user in Step E. As can be seen in FIG. 4, in an alternative embodiment, the sub-process for life experience analysis conducts data analysis of the life experience using artificial intelligence (AI) technology, wherein the AI technology includes machine learning, and wherein the AI technology includes data mining. Further, the method may utilize other technologies, including, but not limited, neural network, data mining, etc.

Figure 5:
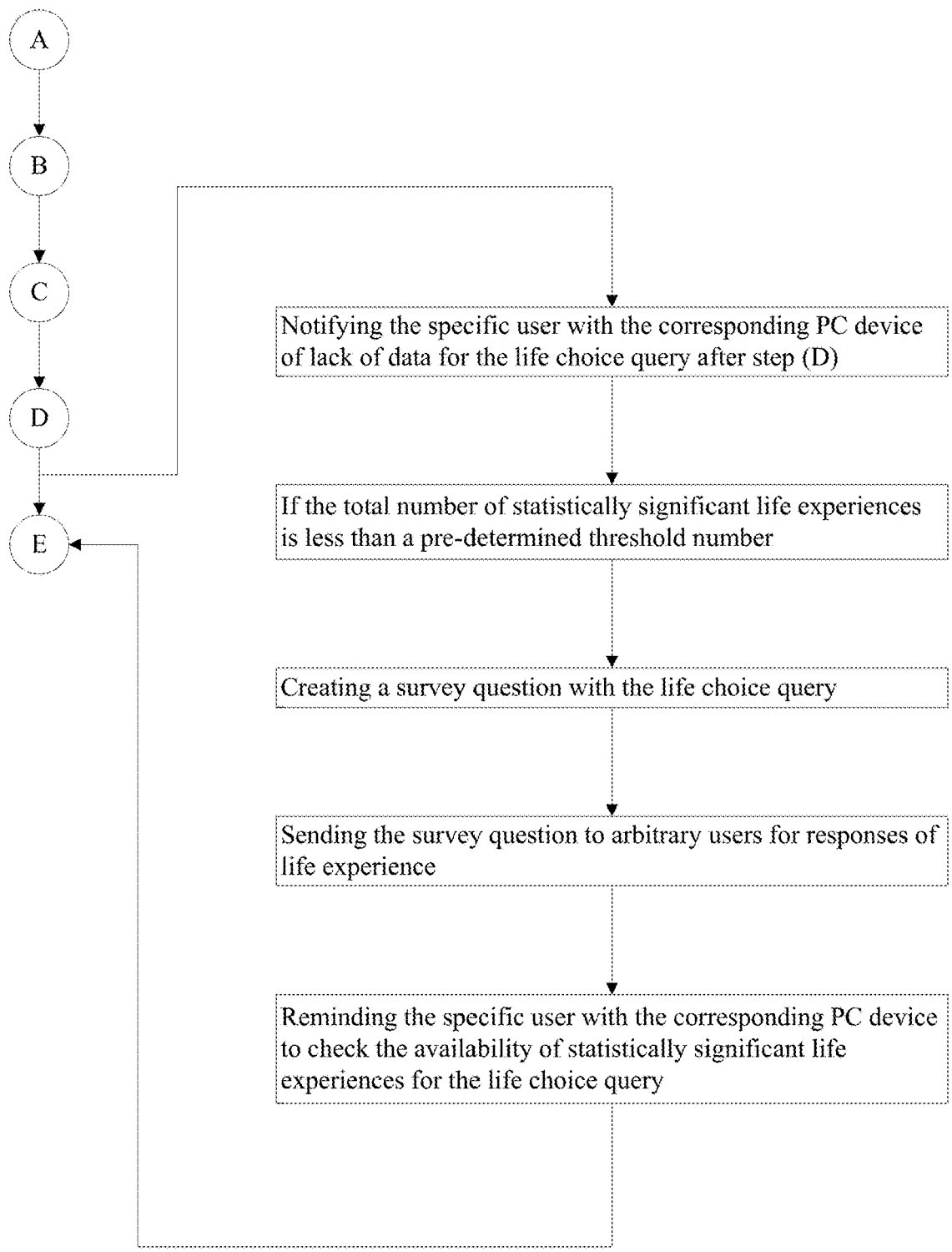
FIG. 5 is a flowchart of a sub-process for notifying a user of lack of data in the method of the present invention.

As can be seen in FIG. 5, the method provides a sub-process for notifying the specific user of lack of data to the query. More specifically, the method notifies the specific user with the corresponding PC device of lack of data for the life choice query after Step D if the total number of statistically significant life experiences is less than a pre-determined threshold number. At the same time, the method creates a survey question with the life choice query and sends the survey question to arbitrary users for responses of life experience. Further, the method reminds the specific user with the corresponding PC device to check the availability of statistically significant life experiences for the life choice query. The method may display survey questions along with a web interface on the corresponding PC device of the specific user, thus allowing the specific user to respond to survey questions that may or may not be stored within the specific user profile. In an alternative embodiment of the present invention, the method allows an arbitrary user to answer a list of survey questions posted by the present invention, which originate from any source such as other user's queries, law enforcement or medical researches queries, or general information needed by any providers. Examples of survey questions would be "what was your G.P.A. in high school?", "how old were you when you had your first car accident?", "have you ever stolen anything?", "how much weight did you gain in college?", etc.

Figure 6:
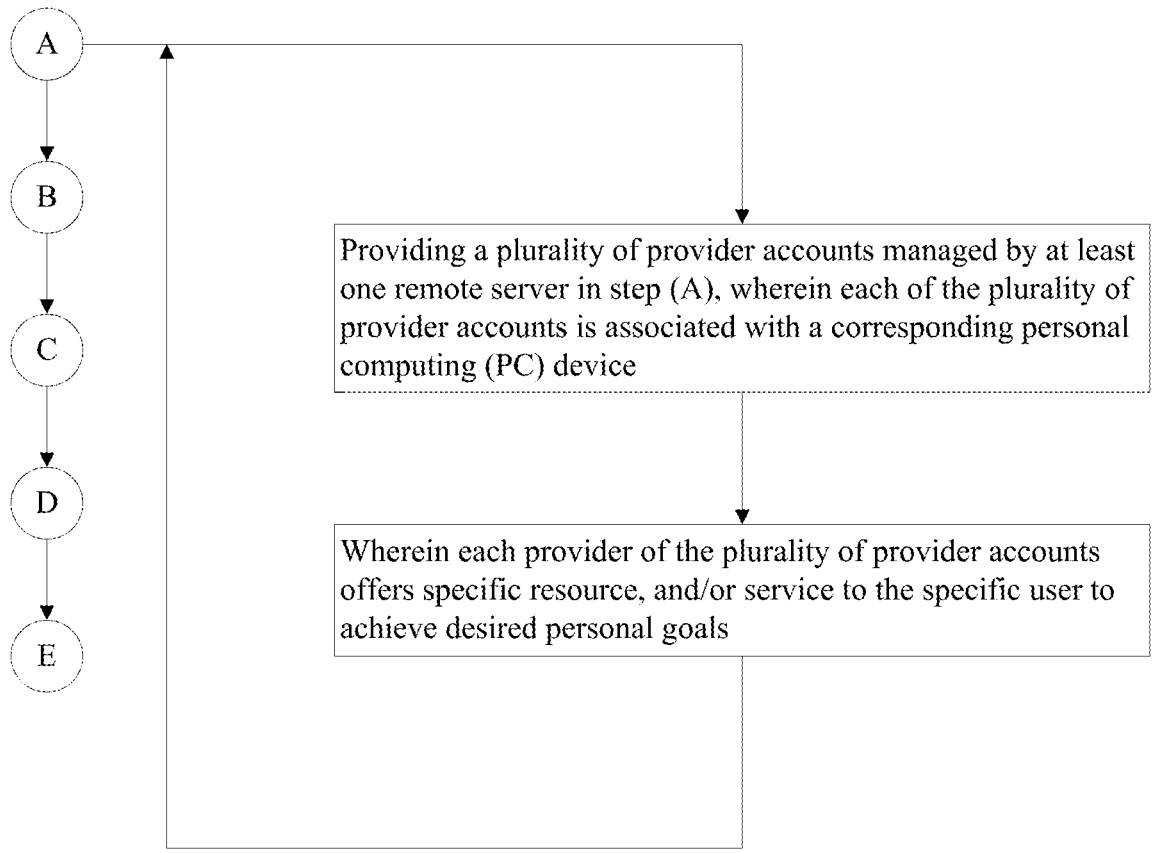
FIG. 6 is a flowchart of a sub-process for providing a plurality of provider accounts by the method of the present invention.
Figure 7:
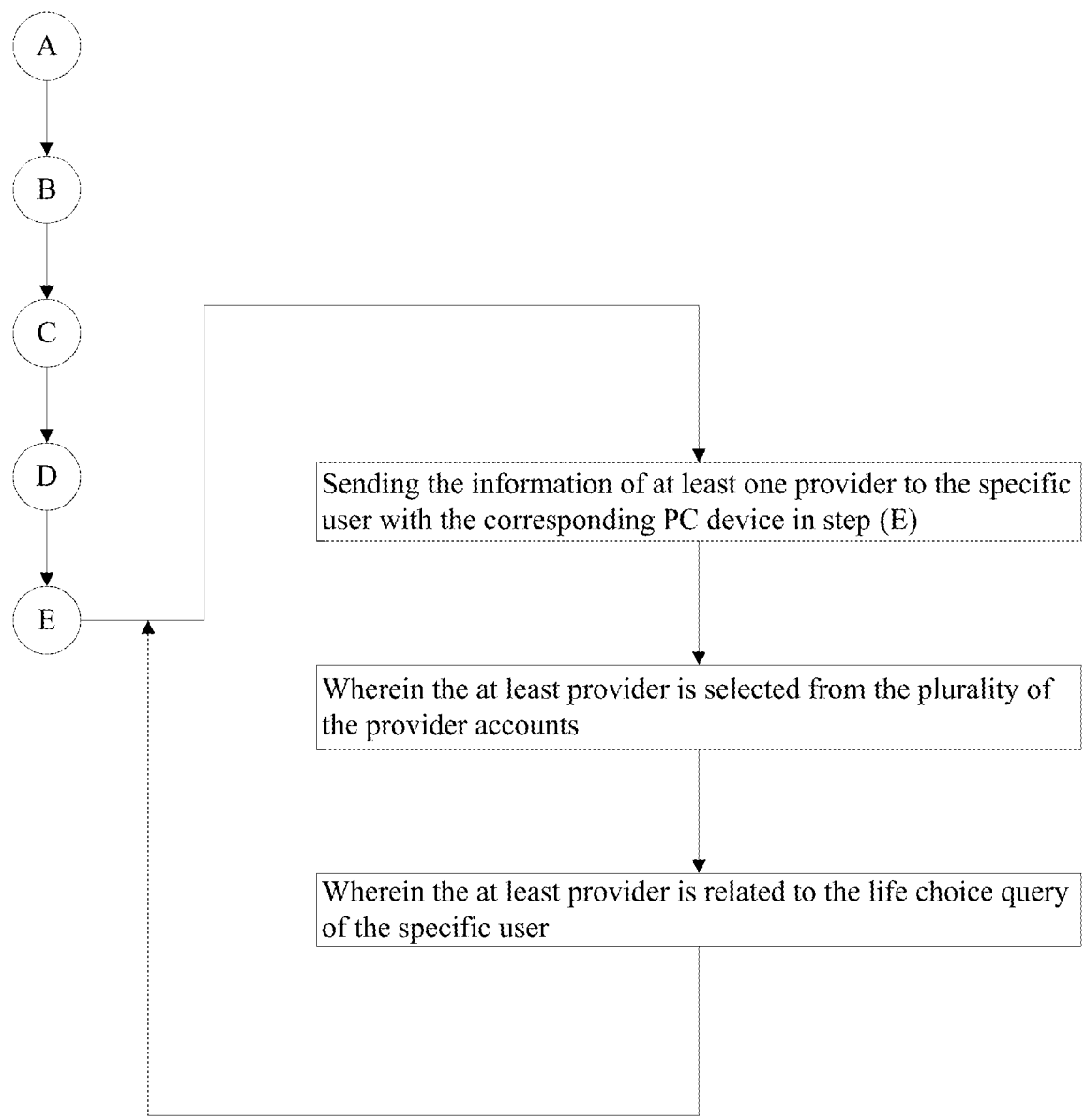
FIG. 7 is a flowchart of a sub-process for sending provider information to the user by the method of the present invention.

As can be seen in FIG. 6, the method provides a sub-process for managing a plurality of provider users. More specifically, the method provides a plurality of provider accounts managed by at least one remote server in Step A, wherein each of the plurality of provider accounts is associated with a corresponding personal computing (PC) device, wherein each provider of the plurality of provider accounts offers specific resource, and/or service to the specific user to achieve desired personal goals. As can be seen in FIG. 7, the method provides a sub-process to link at least one provider with the specific user to assist the specific user in achieving life goals. More specifically, the method sends the information of at least one provider to the specific user with the corresponding PC device in Step E, wherein the at least one provider is selected from the plurality of the provider accounts, and wherein the at least one provider is selected from the plurality of the provider accounts. Thus, the method allows the addition of providers in the query and reporting process so that the providers' information can be included in query search findings under pre-determined conditions, including, but not limited to, if a certain fee is paid in an amount determined by the affiliated social network owners. This fee may be proportional to the level of service requested. Additionally, the providers' information provided to the specific user includes, but is not limited to, contact information, address, category, etc., to identify the providers to the specific user (to follow a fee schedule set up by the social network company). Further, providers are allowed to set up automatically recurring payment options to the social network company for including contact information to users upon matching queries and/or to receive the specific user's contact information if permitted. The method checks specific registered entities including, but not limited to, colleges or companies, to see if those entities are paying advertisers or paying service providers and list contact information of the entities with the results given to the specific user who asked the question/query. If the specific user agrees to send their personal information to the entities, the entities can be sent with the PII (personal identifiable information) of the specific user.

Figure 8:
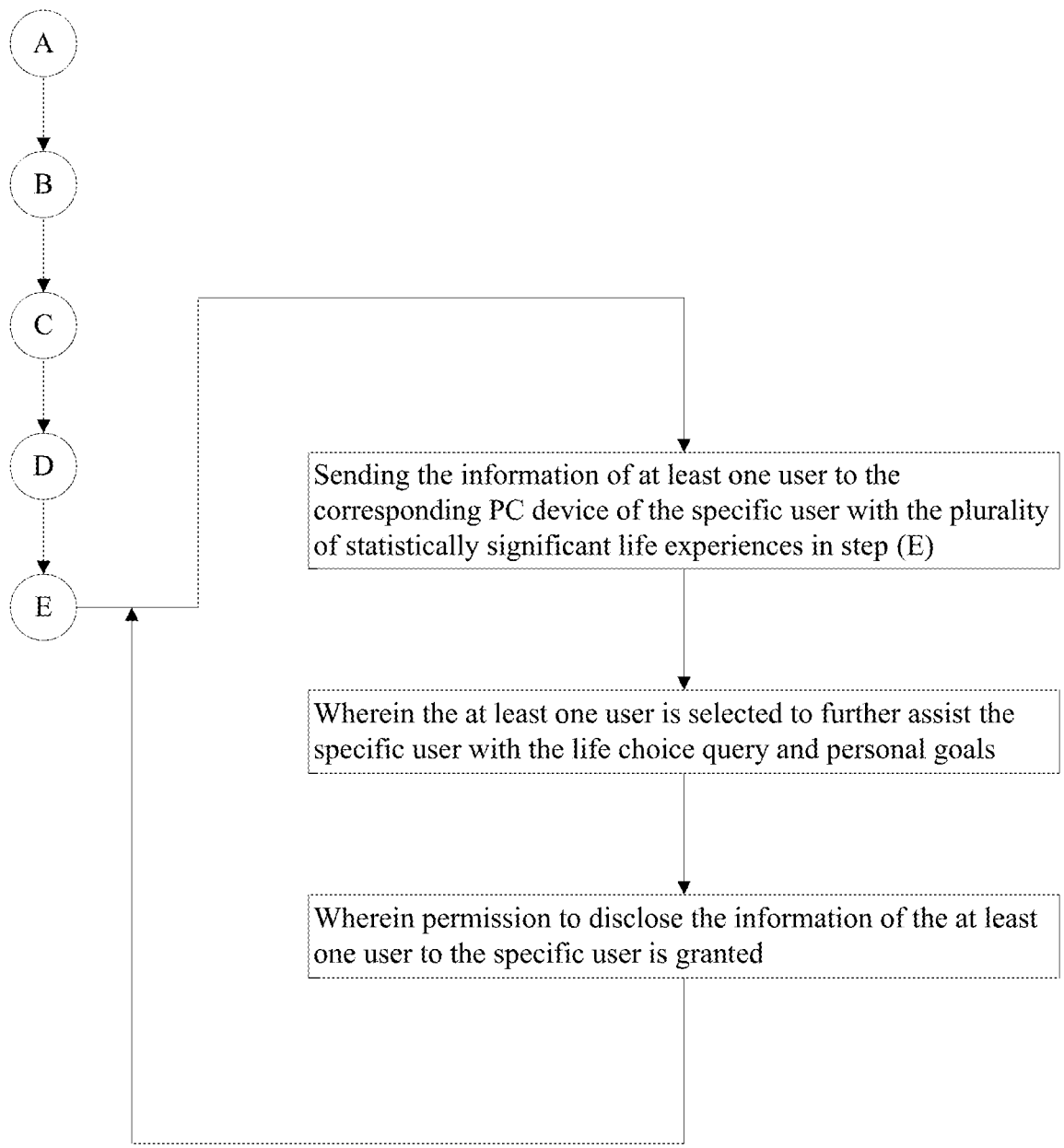
FIG. 8 is a flowchart of a sub-process for linking the user with another user who may help the user achieve personal goals based on search results by the method of the present invention.

As can be seen in FIG. 8, the method provides a sub-process to link at least one user with the specific user to assist the specific user in achieving life goals. More specifically, the method sends the information of at least one user to the corresponding PC device of the specific user with the plurality of statistically significant life experiences in Step E, wherein the at least one user is selected to further assist the specific user with the life choice query and personal goals, and wherein permission to disclose the information of the at least one user is granted.

Figure 9:
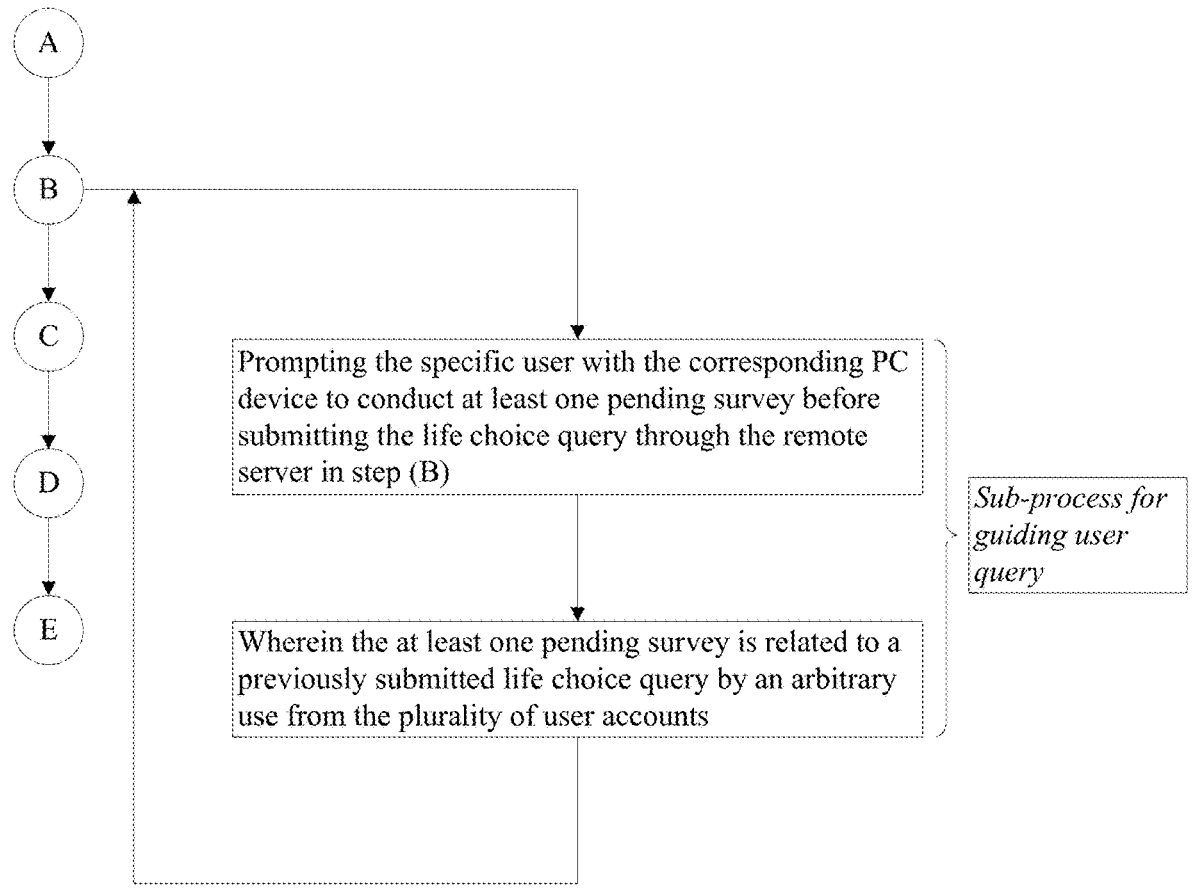
FIG. 9 is a flowchart of a sub-process for guiding the user to enter queries by the method of the present invention.
Figure 10:
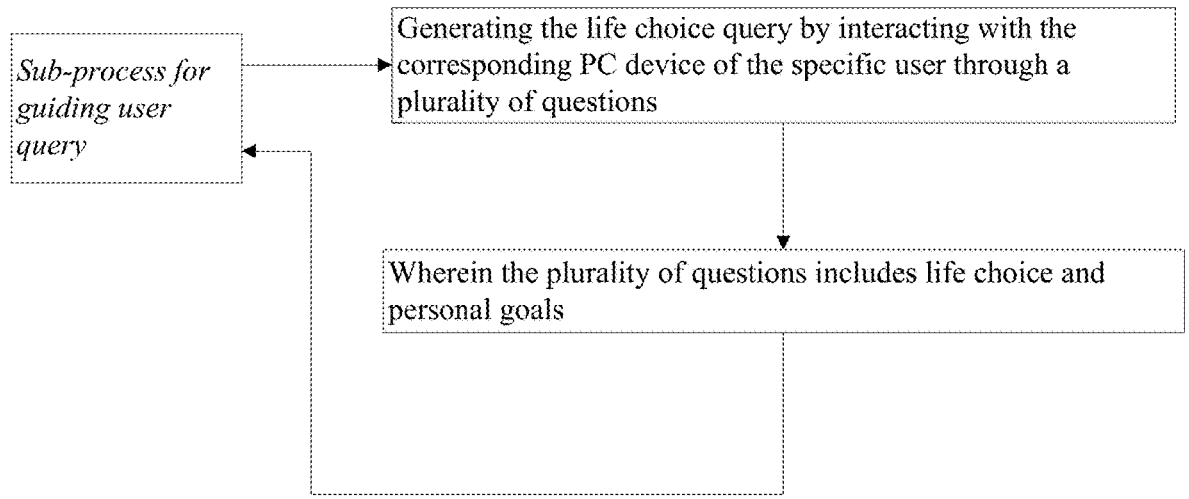
FIG. 10 is a flowchart of an alternative embodiment of the sub-process for guiding the user to enter queries by the method of the present invention.
Figure 11:
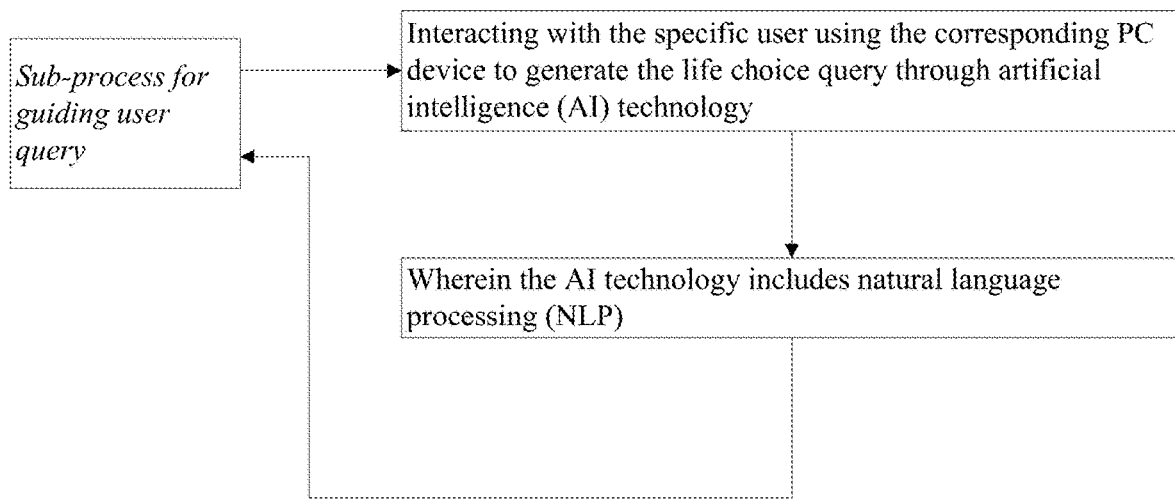
FIG. 11 is a flowchart of another embodiment of the sub-process for guiding the user to enter queries by the method of the present invention.

As can be seen in FIG. 9, the method provides a sub-process to guide the specific user entering life choice query. More specifically, the method prompts the specific user with the corresponding PC device to conduct at least one pending survey before submitting the life choice query through the remote server in Step B, wherein the at least one pending survey is related to a previously submitted life choice query by an arbitrary use from the plurality of user accounts. As can be seen in FIG. 10, in an alternative embodiment of the present invention, the method generates the life choice query by interacting with the corresponding PC device of the specific user through a plurality of questions, wherein the plurality of questions includes life choice and personal goals. As can be seen in FIG. 11, in another embodiment of the present invention, the method interacts with the specific user using the corresponding PC device to generate the life choice query through artificial intelligence (AI) technology, wherein the AI technology includes natural language processing (NLP).

Figure 12:
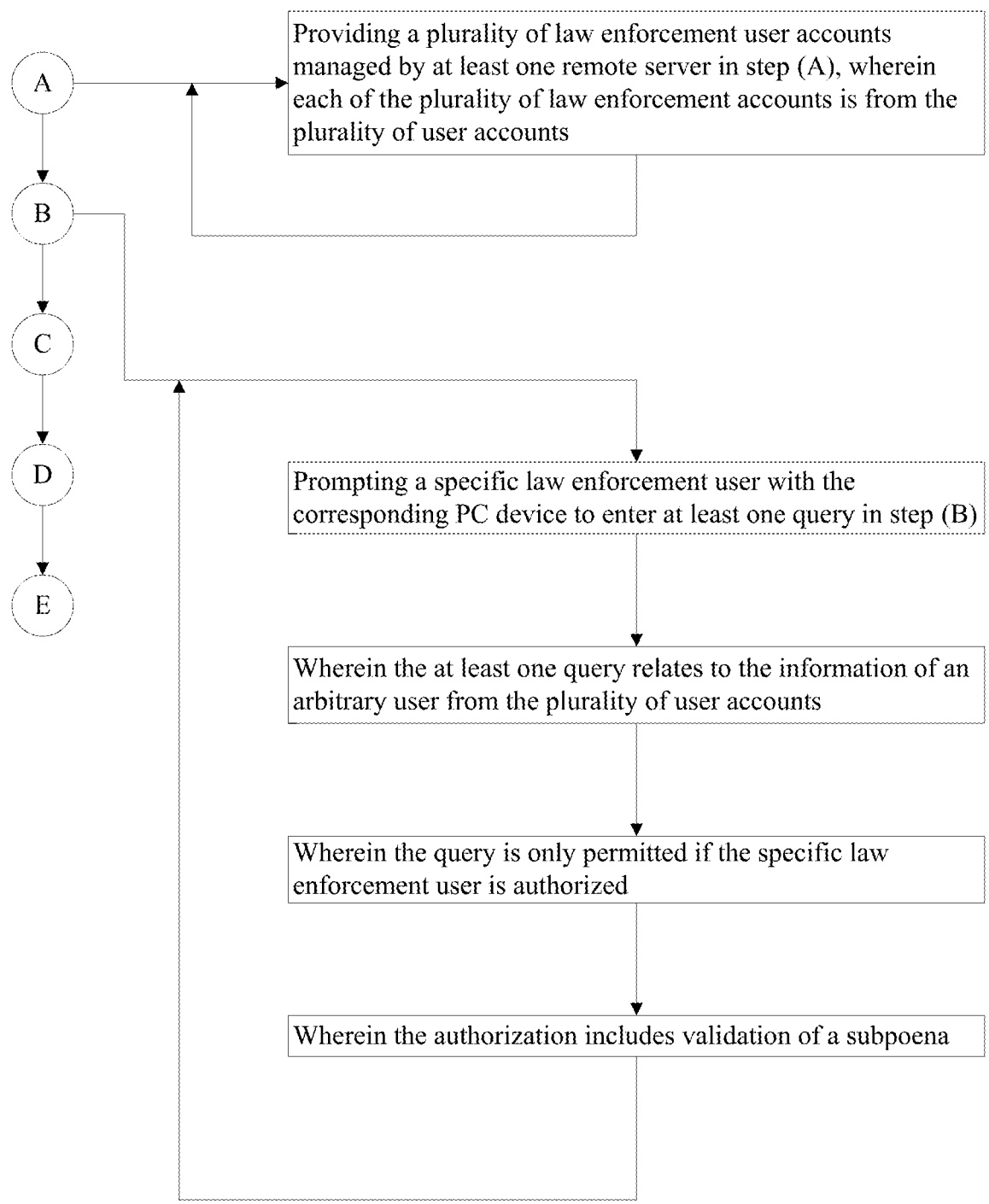
FIG. 12 is a flowchart of a sub-process for providing a law enforcement user to enter queries by the method of the present invention.

As can be seen in FIG. 12, the method provides a sub-process to manage a plurality of law enforcement users to conduct query. More specifically, the method provides a plurality of law enforcement user accounts managed by at least one remote server in Step A, wherein each of the plurality of law enforcement accounts is from the plurality of user accounts. The method then prompts a specific law enforcement user with the corresponding PC device to enter at least one query in Step B, wherein the at least one query relates to the information of an arbitrary user from the plurality of user accounts. Additionally, the query is only permitted if the specific law enforcement user is authorized and the authorization includes validation of a subpoena. Law enforcement users can provide a subpoena for the contact information of a small number of users at one time, based on the profiles/attributes that are queried, assuming a small number of users match the query. Furthermore, the method can connect to separate, secured databases so that the specific law enforcement user can search private databases for anonymous information. Such information can contain databases of law enforcements past-offenders or suspects, information related to potential members financial habits (legal or illegal), etc. related to specific users.

Figure 13:
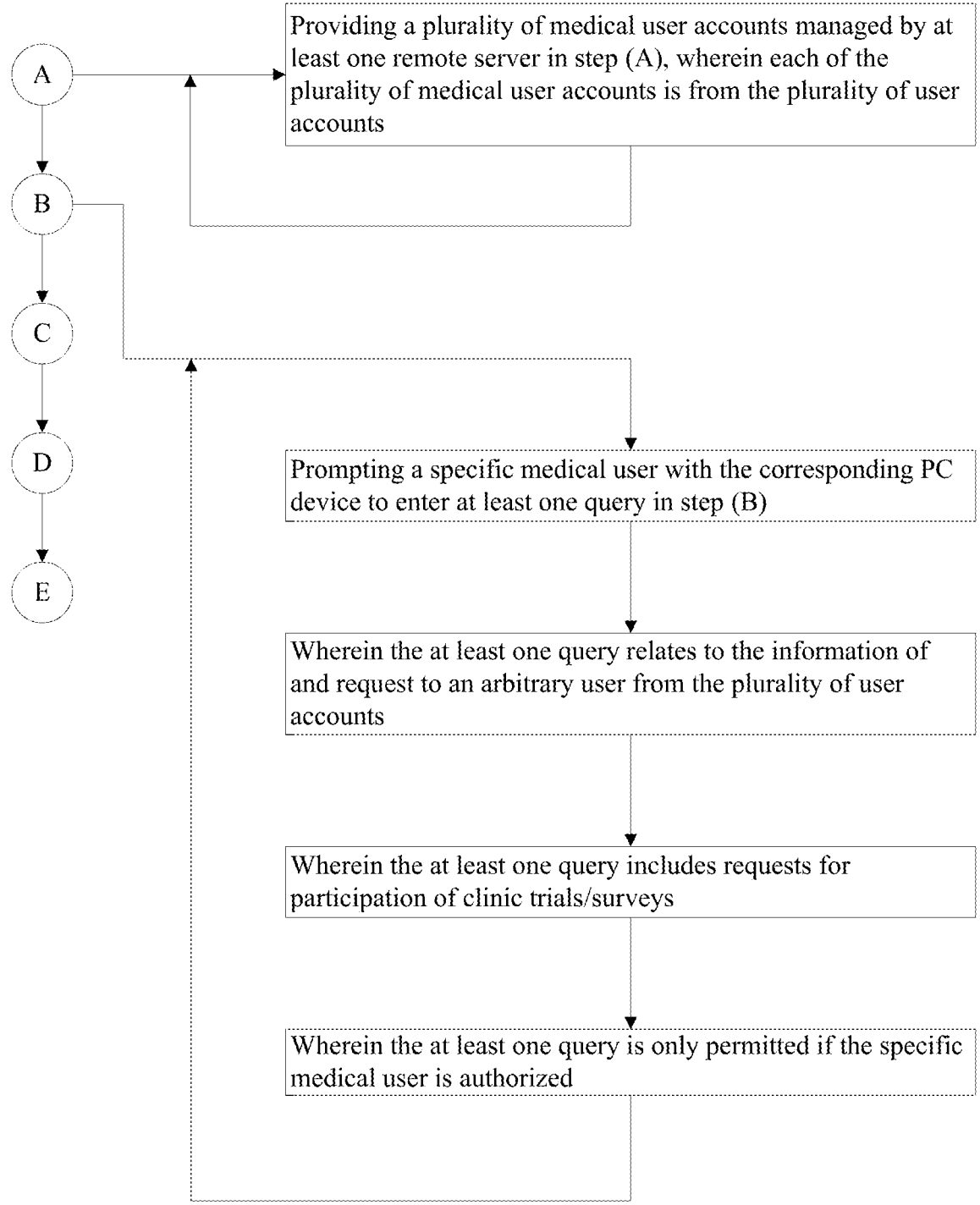
FIG. 13 is a flowchart of a sub-process for providing a medical user to enter queries by the method of the present invention.

As can be seen in FIG. 13, the method provides a sub-process to manage a plurality of medical users to conduct query. More specifically, the method provides a plurality of medical user accounts managed by at least one remote server in Step A, wherein each of the plurality of medical user accounts is from the plurality of user accounts. The method then prompts a specific medical user with the corresponding PC device to enter at least one query in Step B, wherein the at least one query relates to the information of and request to an arbitrary user from the plurality of user accounts. Further, the at least one query includes requests for participation of clinic trials/surveys and the at least one query is only permitted if the specific medical user is authorized. Thus, this sub-process provides a dedicated interface for medical users, including, but not limited to, research users to enter a list of user attributes in the query. Upon running the query search, the method returns the number of users that occur. Medical users can thus request contact from these specific users, while remaining anonymous. The method also allows these medical users to ask additional questions and/or request participation in clinical trials, experimental drug programs, etc. Further, the method can connect to separate, secured databases so that the specific medical user can search private databases for anonymous information. Such information can contain databases medical information or drug prescriptions potentially related to specific user. Thus, the method allows the law enforcement and medical users to select lists of attributes/questions of the social network database to retrieve relevant query results. However, the method of the present invention does not allow access to users' personal information that is prohibited without express consent from the users, or, without a narrow-focused subpoena. Additionally, the method does not allow any user to access PII of other users unless a subpoena, and/or expressed consent is present. Further, questions entered by the law enforcement and medical users that have insufficient number of results to properly return answers can also be posted to the all other users of the system of the present invention.

Figure 14:
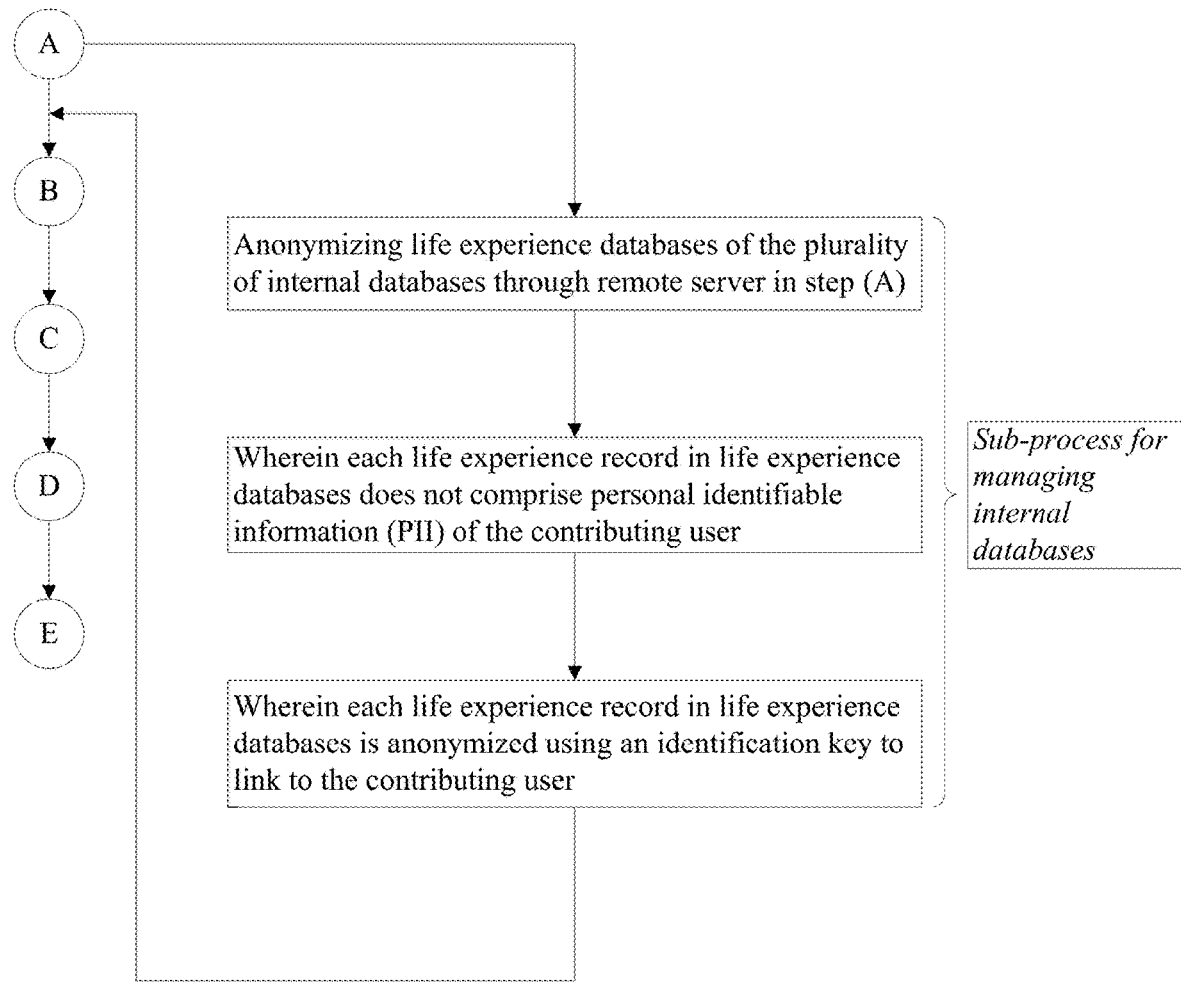
FIG. 14 is a flowchart of a sub-process for managing internal databases by the method of the present invention.

As can be seen in FIG. 14, the method provides a sub-process to manage a plurality of internal databases. More specifically, the method anonymizes life experience databases of the plurality of internal databases through remote server in Step A, wherein each life experience record of life experience databases does not comprise PII of the contributing user, and wherein each life experience record of life experience databases is anonymized using an identification key to link to the contributing user. The method allows users to make a query and search life experience databases of the plurality of internal databases, however, no personal/private information of any contributing users of the life experiences can be shown. First of all, the method separates the user information databases from the life experience databases. Secondly, the method anonymizes the life experience databases using identification keys that do not show any PII of any contributing users. The plurality of databases takes form of a plurality of data server repositories that are retrievable by social network servers. The plurality of databases comprises specific user's PII and contact data required by the present invention with a unique key identifier, user unique key identifier, the associated unique contribution key, anonymized user profile data with a unique contribution key of the specific user, anonymized user answers to any number of member information surveys and survey questions recording the user actual life experiences, not opinion, identified with specific user's unique contribution key, publicly available data, i.e. census data, geographic data, weather data, etc., lists of entities and their relevant information comprising paying service providers, paying advertisers and/or law enforcement contacts, context-sensitive advertisements, entity priorities and service-level parameters, a plurality of member survey questions and flags for each member for each question flagging whether they have answered the question, and a plurality of summarized data to boost performance of the system and provide users with fast response time to anticipated queries. The information received from the plurality of databases is relayed back to the specific user to answer query and is gathered from a statistically relevant number of the specific user's profile, survey answers and/or public data and does not return PII and may utilize performance enhancing information. In the preferred embodiment of the present invention, the plurality of databases comprises a secure database repository for sensitive information.

Figure 15:
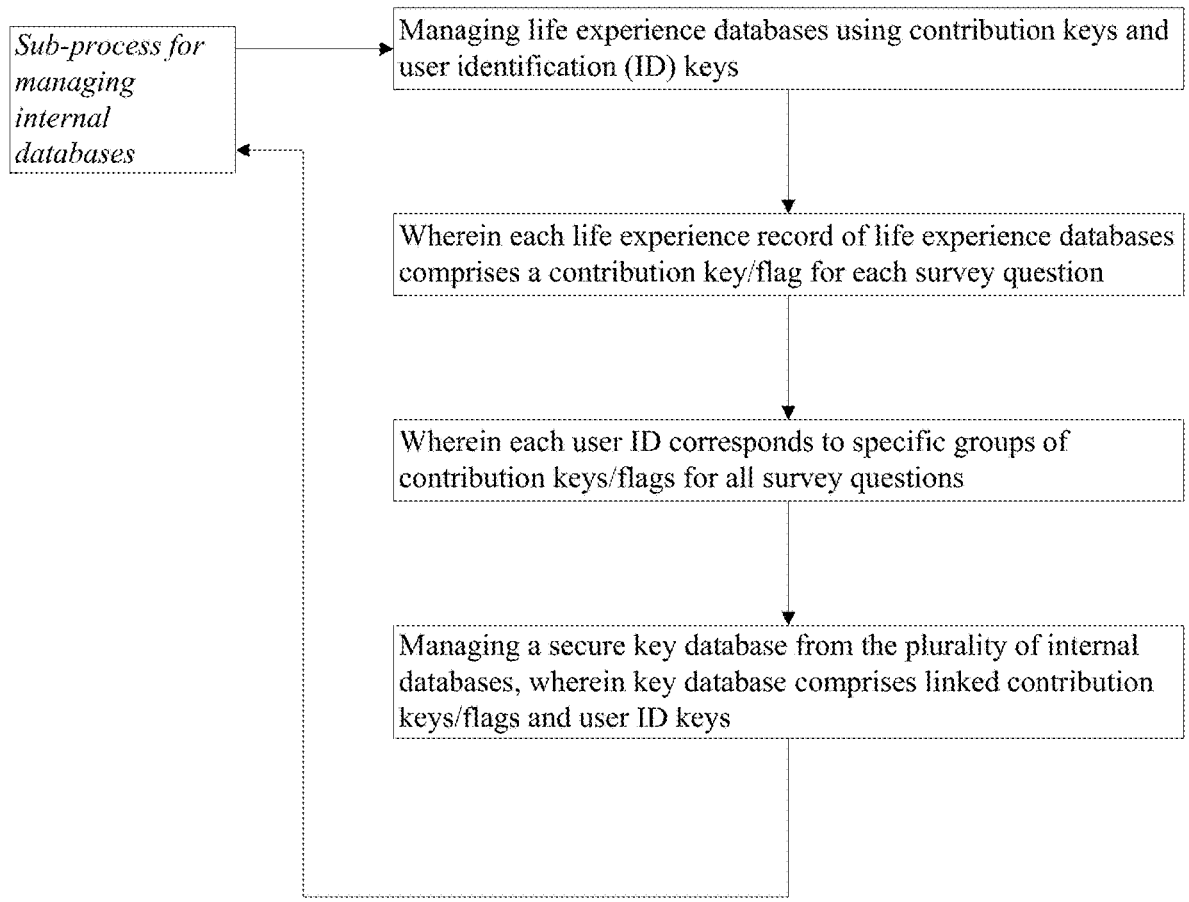
FIG. 15 is a flowchart of an alternative embodiment of the sub-process for managing internal databases by the method of the present invention.
Figure 17:
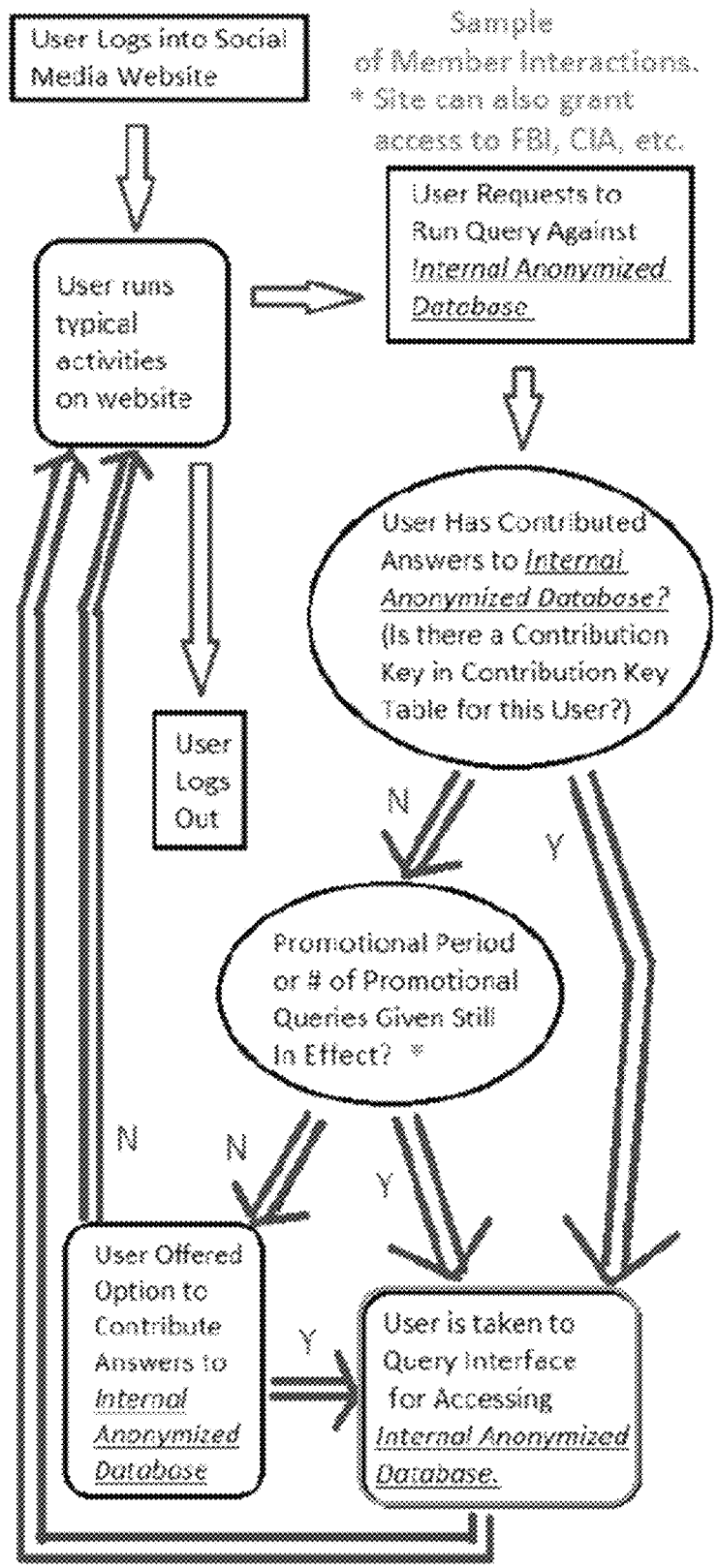
FIG. 17 is a flowchart of an alternative embodiment of the overall process implemented by the method of the present invention.

As can be seen in FIG. 15, in the preferred embodiment of the present invention, the method manages life experience databases using contribution keys and user identification (ID) keys, wherein each life experience record of life experience databases comprises a contribution key/flag for each survey question, and wherein each user ID corresponds to specific groups of contribution keys/flags for all survey questions. Further, the method manages a secure key database from the plurality of internal databases, wherein key database comprises linked contribution keys/flags and user ID keys. As can be seen in FIG. 17 to FIG. 19, in an embodiment of the present invention, the key database may comprise a foreign key or user ID key to the specific user's private information (link) and the unique randomized contribution key that is used in an anonymized life experience database representing the specific user to prevent hackers or others from having PII about the specific user contributing information in the database wherever the contribution key is used. This database allows the method of the present invention to keep track if the specific user has contributed answers to any or all survey questions related to life experiences. This database is also used to identify the specific user whose profile may be identified, or, conditionally be provided to law enforcement users or provider users from queries. An example of life experience databases, as can be seen in FIG. 19, contains contribution keys and answers to at least one survey question asked by any arbitrary user of the present invention or that was derived from the specific user's profile. In this database, no PII is associated with the answers of the specific user.

Figure 16:
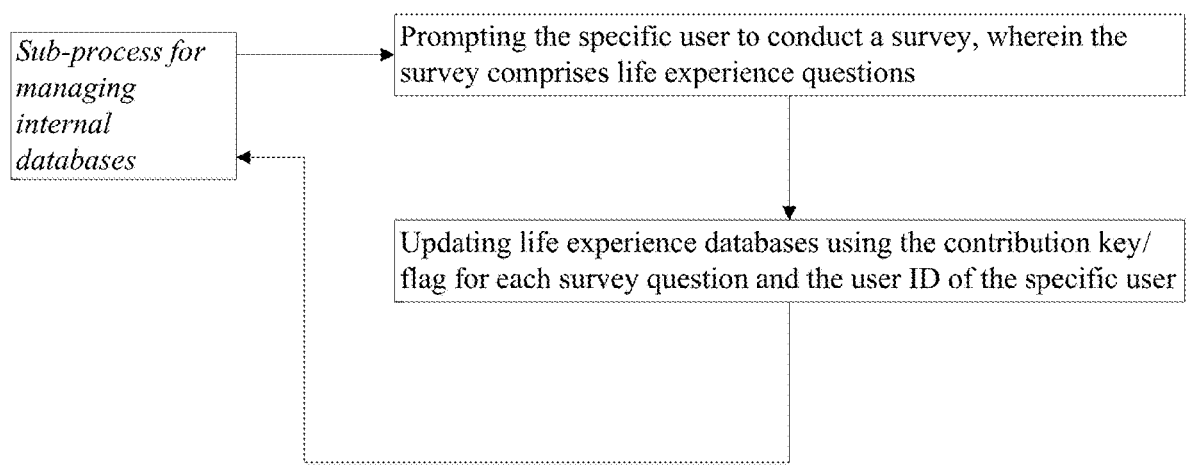
FIG. 16 is a flowchart of another embodiment of the sub-process for managing internal databases by the method of the present invention.

The database can be held in any number of different commercial or private database formats, of which none of them matter to the business logistics. As can be seen in FIG. 16, the method manages internal life experience databases through user input. More specifically, the method prompts the specific user to conduct a survey, wherein the survey comprises life experience questions. Subsequently, the method updates life experience databases using the contribution key/flag for each survey question and the user ID of the specific user once results are received. In another embodiment of the present invention, the method provides a plurality of performance boosting summarized data that is collected on a predetermined frequency including, but not limited to monthly, weekly and/or daily. Such data is gathered by the plurality of servers during off-peak hours and/or may be constantly gathered every few minutes or hours to improve system performance. Further, the method of present invention allows the specific user to link in their own knowledge-based table(s) in the search engine to use in queries.

Although the invention has been explained in relation to its preferred embodiment, it is to be understood that many other possible modifications and variations can be made without departing from the spirit and scope of the invention as hereinafter claimed.

What is claimed is:

1. A method for providing statistically reliable life choice experiences to guide a user to achieve personal goals, the method comprising the steps of:
    (A) providing a plurality of user accounts and a plurality of internal databases managed by at least one remote server, wherein each of the plurality of user accounts is associated with a corresponding personal computing (PC) device;
    (B) prompting a specific user account to submit a life choice query with the corresponding PC device through the remote server, wherein the life choice query may include personal goals;
    (C) searching internal and external databases for life experiences related to the life choice query of the specific user account through the remote server;
    (D) conducting statistically analysis for each life experience with regard to the life choice query of the specific user;
    (E) relaying a plurality of statistically significant life experiences to the specific user account with the corresponding PC device through the remote server; and
    prompting the specific user with the corresponding PC device to conduct at least one pending survey before submitting the life choice query through the remote server in step (B); and
    wherein the at least one pending survey is related to a previously submitted life choice query by an arbitrary use from the plurality of user accounts.

2. The method for providing statistically reliable life choice experiences to guide a user to achieve personal goals as claimed in claim 1, the method comprising the steps of:
    conducting statistical modeling for the life experience data through the remote server in step (D);
    wherein each life experience is analyzed for statistical significance for the life choice query of the specific user; and
    generating the plurality of statistically significant life experiences.

3. The method for providing statistically reliable life choice experiences to guide a user to achieve personal goals as claimed in claim 2, the method comprising the steps of:
    conducting data analysis of the life experience using artificial intelligence (AI) technology;
    wherein the AI technology includes machine learning; and
    wherein the AI technology includes data mining.

4. The method for providing statistically reliable life choice experiences to guide a user to achieve personal goals as claimed in claim 1, the method comprising the steps of:
    notifying the specific user with the corresponding PC device of lack of data for the life choice query after step (D);
    if the total number of statistically significant life experiences is less than a pre-determined threshold number;
    creating a survey question with the life choice query;
    sending the survey question to arbitrary users for responses of life experience; and
    reminding the specific user with the corresponding PC device to check the availability of statistically significant life experiences for the life choice query.

5. The method for providing statistically reliable life choice experiences to guide a user to achieve personal goals as claimed in claim 1, the method comprising the steps of:
    providing a plurality of provider accounts managed by at least one remote server in step (A), wherein each of the plurality of provider accounts is associated with a corresponding personal computing (PC) device; and
    wherein each provider of the plurality of provider accounts offers specific resource, and/or service to the specific user to achieve desired personal goals.

6. The method for providing statistically reliable life choice experiences to guide a user to achieve personal goals as claimed in claim 5, the method comprising the steps of:
    sending the information of at least one provider to the specific user with the corresponding PC device in step (E); and
    wherein the at least one provider is selected from the plurality of the provider accounts.

7. The method for providing statistically reliable life choice experiences to guide a user to achieve personal goals as claimed in claim 1, the method comprising the steps of:
    sending the information of at least one user to the corresponding PC device of the specific user with the plurality of statistically significant life experiences in step (E);
    wherein the at least one user is selected to further assist the specific user with the life choice query and personal goals; and
    wherein permission to disclose the information of the at least one user is granted.

8. The method for providing statistically reliable life choice experiences to guide a user to achieve personal goals as claimed in claim 1, the method comprising the steps of:
    generating the life choice query by interacting with the corresponding PC device of the specific user through a plurality of questions; and
    wherein the plurality of questions includes life choice and personal goals.

9. The method for providing statistically reliable life choice experiences to guide a user to achieve personal goals as claimed in claim 1, the method comprising the steps of:
    interacting with the specific user using the corresponding PC device to generate the life choice query through artificial intelligence (AI) technology; and
    wherein the AI technology includes natural language processing (NLP).

10. The method for providing statistically reliable life choice experiences to guide a user to achieve personal goals as claimed in claim 1, the method comprising the steps of:
providing a plurality of law enforcement user accounts managed by at least one remote server in step (A), wherein each of the plurality of law enforcement accounts is from the plurality of user accounts;
prompting a specific law enforcement user with the corresponding PC device to enter at least one query in step (B);
wherein the at least one query relates to the information of an arbitrary user from the plurality of user accounts;
wherein the query is only permitted if the specific law enforcement user is authorized; and
wherein the authorization includes validation of a subpoena.

11. The method for providing statistically reliable life choice experiences to guide a user to achieve personal goals as claimed in claim 1, the method comprising the steps of:
providing a plurality of medical user accounts managed by at least one remote server in step (A), wherein each of the plurality of medical user accounts is from the plurality of user accounts;
prompting a specific medical user with the corresponding PC device to enter at least one query in step (B);
wherein the at least one query relates to the information of and request to an arbitrary user from the plurality of user accounts;
wherein the at least one query includes requests for participation of clinic trials/surveys; and
wherein the at least one query is only permitted if the specific medical user is authorized.

12. The method for providing statistically reliable life choice experiences to guide a user to achieve personal goals as claimed in claim 1, the method comprising the steps of:
anonymizing life experience databases of the plurality of internal databases through remote server in step (A);
wherein each life experience record in life experience databases does not comprise private information of the contributing user; and
wherein each life experience record in life experience databases is anonymized using an identification key to link to the contributing user.

13. The method for providing statistically reliable life choice experiences to guide a user to achieve personal goals as claimed in claim 12, the method comprising the steps of:
managing life experience databases using contribution keys and user identification (ID) keys;
wherein each life experience record of life experience databases comprises a contribution key/flag for each survey question;
wherein each user ID corresponds to specific groups of contribution keys/flags for all survey questions; and
managing a secure key database from the plurality of internal databases, wherein key database comprises linked contribution keys/flags and user ID keys.

14. The method for providing statistically reliable life choice experiences to guide a user to achieve personal goals as claimed in claim 12, the method comprising the steps of:
prompting the specific user to conduct a survey, wherein the survey comprises life experience questions; and
updating life experience databases using the contribution key/flag for each survey question and the user ID of the specific user.

* * * * *